(12) United States Patent
Ninh

(10) Patent No.: US 12,016,549 B2
(45) Date of Patent: Jun. 25, 2024

(54) CONTINUOUS LOOP SUTURE ASSEMBLY AND RELATED SURGICAL TECHNIQUES

(71) Applicant: Christopher Ninh, Irvine, CA (US)

(72) Inventor: Christopher Ninh, Irvine, CA (US)

( * ) Notice: Subject to any disclaimer, the term of this patent is extended or adjusted under 35 U.S.C. 154(b) by 205 days.

(21) Appl. No.: 17/736,006

(22) Filed: May 3, 2022

(65) Prior Publication Data
US 2023/0190256 A1 Jun. 22, 2023

Related U.S. Application Data

(63) Continuation of application No. 17/553,646, filed on Dec. 16, 2021, now Pat. No. 11,350,926.

(51) Int. Cl.
*A61B 17/04* (2006.01)

(52) U.S. Cl.
CPC ...... *A61B 17/0401* (2013.01); *A61B 17/0485* (2013.01); *A61B 2017/0412* (2013.01); *A61B 2017/0414* (2013.01); *A61B 2017/044* (2013.01)

(58) Field of Classification Search
CPC ............ A61B 17/0401; A61B 17/0485; A61B 2017/0412; A61B 2017/0414; A61B 2017/044
See application file for complete search history.

(56) References Cited

U.S. PATENT DOCUMENTS

| | | | |
|---|---|---|---|
| 7,329,272 B2 | 2/2008 | Burkhart | |
| 8,118,836 B2 | 2/2012 | Denham et al. | |
| 8,652,172 B2 | 2/2014 | Denham et al. | |
| 8,882,801 B2 | 11/2014 | DiMatteo et al. | |
| 8,961,560 B2 | 2/2015 | Avelar et al. | |
| 9,161,748 B2 | 10/2015 | West, Jr. | |
| 9,284,668 B2 | 3/2016 | Johnson | |
| 9,597,068 B2 | 3/2017 | Sengun | |
| 9,615,821 B2 | 4/2017 | Sullivan | |
| 9,737,293 B2 | 8/2017 | Sengun et al. | |
| 10,034,663 B1 | 7/2018 | Nason et al. | |
| 10,092,285 B2 | 10/2018 | Graul et al. | |
| 10,245,019 B2 | 4/2019 | Sengun | |
| 10,327,755 B2 | 6/2019 | Feezor et al. | |
| 10,335,136 B2 * | 7/2019 | Dooney, Jr. | A61B 17/06166 |
| 10,631,848 B2 | 4/2020 | Sengun et al. | |
| 11,224,417 B2 | 1/2022 | Nason et al. | |
| 2006/0282081 A1 | 12/2006 | Fanton et al. | |
| 2007/0219558 A1 | 9/2007 | Deutsch | |
| 2008/0208252 A1 | 8/2008 | Holmes | |
| 2008/0312689 A1 | 12/2008 | Denham et al. | |

(Continued)

*Primary Examiner* — Phong Son H Dang
(74) *Attorney, Agent, or Firm* — Roland J. Tong

(57) ABSTRACT

A repair suture consists of a strand of suture material formed into a continuous loop. One end of the loop may be thicker than the other. The repair suture may be part of a suture assembly including the repair suture, a linking suture having a looped end and a straight end, and a suture anchor. The suture anchor may have a suture bridge that divides the cross-sectional area of the interior of the anchor into two unequal sections. The suture assembly may be used to create luggage tag configurations for repairing tissue or for attaching tissue to bone. In a double-row method with medial row compression, loose suture ends from the medial row are inserted into a lateral row anchor having a proximal anchor body, a distal tip, and internal locking elements for locking the distal tip to the proximal anchor body.

11 Claims, 11 Drawing Sheets

(56) References Cited

U.S. PATENT DOCUMENTS

| | | |
|---|---|---|
| 2012/0158051 A1 | 6/2012 | Foerster |
| 2015/0164497 A1 | 6/2015 | Callison et al. |
| 2019/0343507 A1 | 11/2019 | Chavan et al. |

* cited by examiner

CONTINUOUS LOOP SUTURE ASSEMBLY AND RELATED SURGICAL TECHNIQUES

CROSS-REFERENCE TO RELATED APPLICATIONS

This application is a continuation of U.S. nonprovisional patent application Ser. No. 17/553,646, filed Dec. 16, 2021, the entire contents of which are incorporated herein by reference.

BACKGROUND OF THE INVENTION

1. Field of the Invention

The present disclosure relates in general to soft tissue repair surgery, and more particularly, to a suture and anchor system for attaching soft tissue to bone.

2. Background Art

Soft tissues such as ligaments and tendons can sometimes detach from their associated bones as a result of repeated stress, acute trauma, or degeneration due to age. Partial detachment can often be managed with a combination of treatments including physical therapy, rest, acetaminophen, anti-inflammatory drugs, and steroids. However, full detachment usually requires surgery.

One common soft-tissue-to-bone reattachment procedure is rotator cuff repair, which involves reattaching a rotator cuff tendon to the head of the humerus. Rotator cuff repair can be fully open, arthroscopic, or mini-open, and can be performed using knotted or knotless techniques. A typical knotted repair technique involves loading a suture strand having two free ends into a suture anchor, implanting the suture anchor in a bone below a torn rotator cuff tendon, passing the two free ends of the suture in a bottom-to-top direction through the tendon, and then using the free ends to tie a knot securing the tendon to the bone. In a knotless repair technique, the two free ends of the suture are, instead of being tied, passed through the distal end of a second suture anchor, which is then be implanted in the bone, trapping the suture ends in an interference fit between the anchor and the bone.

Many surgeons prefer knotless repair techniques since they require less technical expertise and are less time-consuming than knotted repair techniques. In addition, knots can be bulky and can cause impingement of the tendon on the bone. However, knotless techniques can also be problematic since they allow relative movement between the tendon and the suture. In addition, suture slippage can occur if the interference fit between a knotless suture anchor and the surrounding bone is not sufficiently tight, as is frequently the case in patients having diminished bone density due to age or disease. Another problem of both knotted and knotless repair techniques is anchor pullout, which can occur as a result of trauma or diminished bone density. Still another problem is the formation of undesirable flaps or folds known as "dog-ear" lesions between sutures or knots, which can result in impingement and compromise the quality of repair.

These and other problems are addressed by this disclosure as summarized below.

SUMMARY OF THE INVENTION

In one aspect of the present disclosure, a repair suture comprises a strand of suture material formed into a continuous loop. In one example, the strand is a thin filament. In another example, the strand is a tape. In yet another example, the strand has a varying diameter.

The loop includes a first end, a second end, and two sides extending between the first and second ends. In the example using the varying diameter strand, the thinnest portion of the strand is at the first end of the loop, and the thickest portion of the strand is at the second end of the loop.

A method for repairing tissue according to the present disclosure comprises: 1) folding a suture loop into a U-shape having a first end bight, a second end bight, and a central bight; 2) passing the first end bight through the tissue at a first location, passing the second end bight through the tissue at a second location; 3) forming a luggage tag configuration with the two end bights; and 4) securing the luggage tag configuration against the tissue with an auxiliary locking mechanism. Examples of auxiliary locking mechanism that may be used include a knot, an interference fit between a portion of the suture loop and an internal bridge in a hard suture anchor, pressure exerted by the contact surface of a soft suture anchor against the surrounding bone, or an internal lock in a lateral anchor.

In one example of the method, the luggage tag configuration is formed by passing the first end bight through the second end bight.

In an alternate example of the method, the luggage tag configuration is formed by cutting through the first end bight to form separate limbs, and then extending one of the limbs through the second end bight. A locking knot is formed by tying the two limbs together.

In one aspect of the method, the loop includes a first end, a second end, and two sides extending between the first and second ends, and the strand has a thickness which increases from a minimum thickness at the first end to a maximum thickness at the second end. The thickest part of the strand, which is located in the second end bight when the loop has been folded, creates an interference lock with the internal anchor bridge when luggage-tagged.

In one example, the suture loop is positioned within a suture anchor having a proximal end, a distal end, and a suture engagement feature disposed at the distal end. The central bight of the suture loop extends around the suture engagement feature, and the first and second end bights extend proximally through the proximal end of the suture anchor.

In another example, the suture loop extends through an all suture anchor configured to expand radially outwardly and exert a contact force against surrounding bone when deployed.

In another aspect of the disclosure, a suture assembly includes a medial anchor, a repair suture, and a linking suture. The medial anchor has a first side, a second side, and a proximal end. The repair suture is formed as a continuous loop and doubled on itself to form a first end bight, a second end bight, and a central bight, and positioned in the medial anchor such that the first end bight extends out of the proximal end of the medial anchor on the first side thereof, and the second end bight extends out of the proximal end of the medial anchor on the second side thereof. The linking suture has a looped end joined to a straight end by an intermediate portion, and is doubled on itself within the medial anchor such that the straight end extends out of the proximal end of the medial anchor on the first side thereof, and the looped end extends out of the proximal end of the medial anchor on the second side thereof.

In one example of the suture assembly, the loop is formed from a strand of suture material and includes a first end, a second end, and two sides extending between the first and second ends. The strand has a thickness which increases along each side from a minimum thickness at the first end to a maximum thickness at the second end.

In one aspect of the disclosure, a suture anchor has an open proximal end that communicates with an inner cannulation. A suture engagement feature extends across the inner cannulation and divides the cross-sectional area of the inner cannulation into two sections, wherein one section has a cross-sectional area equal to about 60% of the cross-sectional area of the whole inner cannulation at that location, and the other section has a cross-sectional area equal to about 40% of the cross-sectional area of the whole inner cannulation at that location.

A double-row method of attaching tissue to bone according to the present disclosure comprises implanting two suture assemblies as described above into two medial locations in a bone below a detached tissue and using the end bights of the repair sutures in the two suture assemblies to create luggage tag configurations before securing the tissue to the bone at the two medial locations. One end bight in each luggage tag configuration forms the base of the luggage tag, and the other end bight is cut, dividing it into two limbs. The straight end of the linking suture of the second suture assembly is inserted through the loop of the linking suture of the first suture assembly, and the straight end of the first suture assembly is pulled, drawing the linking suture assembly into the tissue at the first location, and creating a medial bar connecting the two luggage tag configurations. One of the cut limbs from the each of the luggage tag configurations plus the straight end of the linking suture of the first suture assembly is inserted into a first lateral anchor, which is then implanted in a first lateral location in the bone, trapping the sutures in an interference fit between the lateral anchor and the bone. The other cut limb from each luggage tag configuration plus the looped end of the linking suture is inserted into a second lateral anchor, which is then implanted in a second lateral location in the bone.

In one aspect of the double-row method, each repair suture is formed from a strand of suture material and includes a first end, a second end, and two sides extending between the first and second ends. The strand has a thickness which increases from a minimum thickness at the first end to a maximum thickness at the second end. The maximum thickness of the strand is preferably located in the second end bight, and the second suture assembly is preferably positioned such that the straight end of the linking suture of the second suture assembly faces the looped end of the linking suture of the first suture assembly.

In another aspect of the double-row method, the first lateral anchor comprises a proximal anchor body, a distal tip, and internal locking elements configured to lock the distal tip to the proximal anchor body when the lateral anchor is implanted in a bone. The distal tip has a retaining feature configured to receive the free ends of the repair sutures from the medial row, and a suture engagement feature configured to engage a pair of stay sutures. The distal tip may also include a pointed distal end configured to facilitate insertion into bone, and a pair of spikes extending proximally and radially outwardly from the pointed distal end.

In one example of the method, the internal locking elements of the first lateral anchor may comprise mating threads formed in a distal portion of the inner cannulation of the proximal anchor body and on a proximal portion of the distal tip.

In another aspect of the disclosure, a lateral suture anchor comprises a proximal anchor body having an open proximal body, a distal tip including an eyelet configured to receive an end of a repair suture, and internal locking elements configured to lock the distal tip to the proximal anchor body when the lateral anchor is implanted in a bone. At least one stay suture extends proximally from a suture engagement feature in the distal tip and continues outwardly through the open proximal end of the anchor body.

In one example, the internal locking elements of the lateral suture anchor comprise mating threads formed in a distal portion of the inner cannulation of the proximal anchor body and on a proximal portion of the distal tip.

In another example, the suture engagement feature comprises an apertured tab extending proximally from a proximal end of the distal tip, and the stay suture extends through the apertured tab.

In one example, the stay suture includes a looped end, a straight end, and an intermediate portion. and is doubled over itself so that the intermediate portion extends through the apertured tab, and the looped and straight ends extend proximally through the open proximal end of the proximal anchor body.

DETAILED DESCRIPTION OF THE PREFERRED EMBODIMENT(S)

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
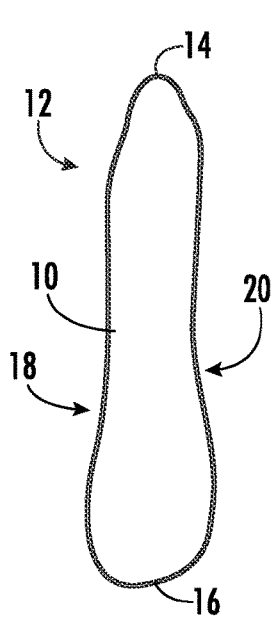
FIG. 1 shows a continuous loop suture according to a first example.
Figure 2:
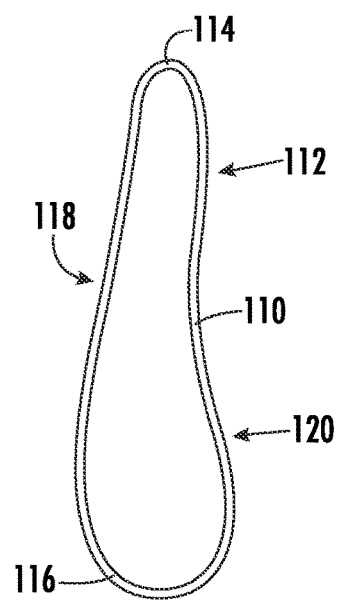
FIG. 2 shows a continuous loop suture according to a second example.
Figure 3:
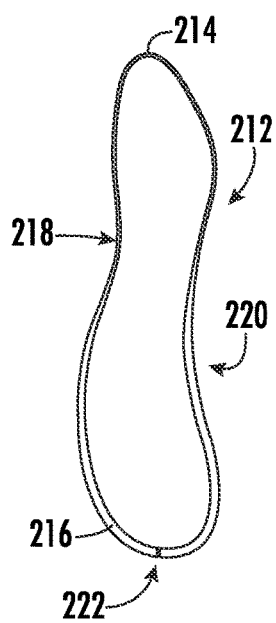
FIG. 3 shows a continuous loop suture according to a third example

FIGS. 1-3 show three examples of a continuous loop suture according to the present invention. FIG. 1 shows a thin strand of suture wire 10 formed into a continuous loop 12 having a first end 14, a second end 16, and two sides 18, 20. The suture wire may be formed of any natural or synthetic suture material such as silk, nylon, polyester, ultra-high molecular weight polyethylene (UHMWPE) or Poly (ethylene terephthalate), or combinations thereof, and may be monofilament or multifilament, absorbable or non-absorbable, coated or uncoated, braided or unbraided, depending on application and on the surgeon's preferences. For rotator cuff repair, #2 UHMWPE sutures are recommended.

FIG. 2 shows a strand of suture tape 110 formed into a continuous loop 112 having a first end 114, a second end 116, and two sides 118, 120. The suture tape 110 may be made of the same materials as suture wire 10, but is flat-braided and may have a thickness of between about 0.9 and about 2.0 mm.

FIG. 3 shows a continuous suture loop 212 having a first end 214, a second end 216, and two sides 218, 220. The loop may be made of any of the suture materials listed above and has a thickness which increases along both sides 218, 220, from a minimum at the first end 214 to a maximum at the second end 216. Laser markings 222 or other indicia may be provided at the second end 216 to help the surgeon quickly find the thickest part of the suture loop. In one example, the thin end 214 of the loop may have the thickness of a #2 suture, and the thick end 216 may have the thickness of suture tape, for instance up to 1.5 to 2 mm.

Figure 4A:
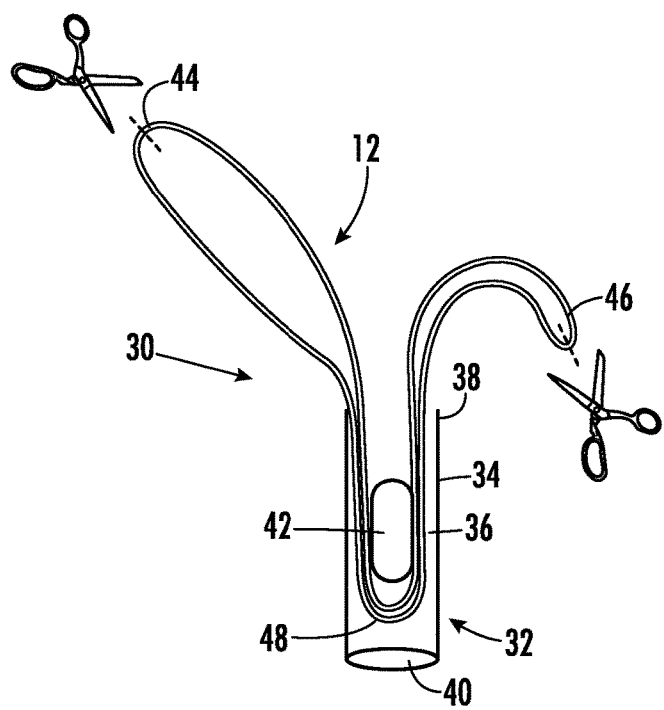
FIG. 4A represents a suture assembly according to one example.

FIG. 4A is a schematic drawing showing a suture assembly 30 including a single suture loop 12 and suture anchor 32. The suture anchor 32, which may be made of any conventional suture anchor material such as titanium, Poly-L-lactic acid (PLLA), or polyetheretherketone (PEEK), includes an anchor body 34 having an inner cannulation 36, an open proximal end 38, a distal end 40, and a suture engagement feature 42 disposed near the distal end 40. The suture loop 12, which may be formed of suture wire as in FIG. 1, suture tape as in FIG. 2, or a varying-width strand as in FIG. 3, has been doubled on itself to form a first end bight 44, second end bight 46, and a central bight 48, and is positioned in the inner cannulation 36 of the anchor 32 such that each of the end bights 44, 46 extends in a proximal direction through the open proximal end 38 of the anchor, and the central bight 48 extends around the suture engagement feature 42, which may also be referred to as a suture bridge. At some point, certain surgical techniques may require cutting through one or both end bights 44, 46 to divide the loop into separate strands, as will shortly be described below.

Figure 4B:
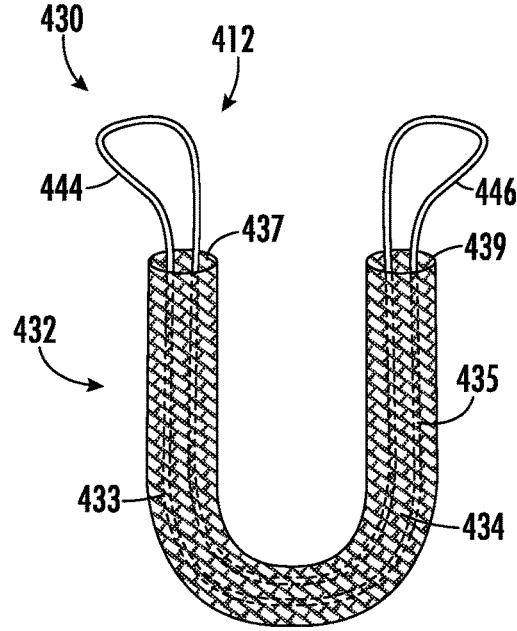
FIG. 4B represents a suture assembly according to another example.
Figure 10A:
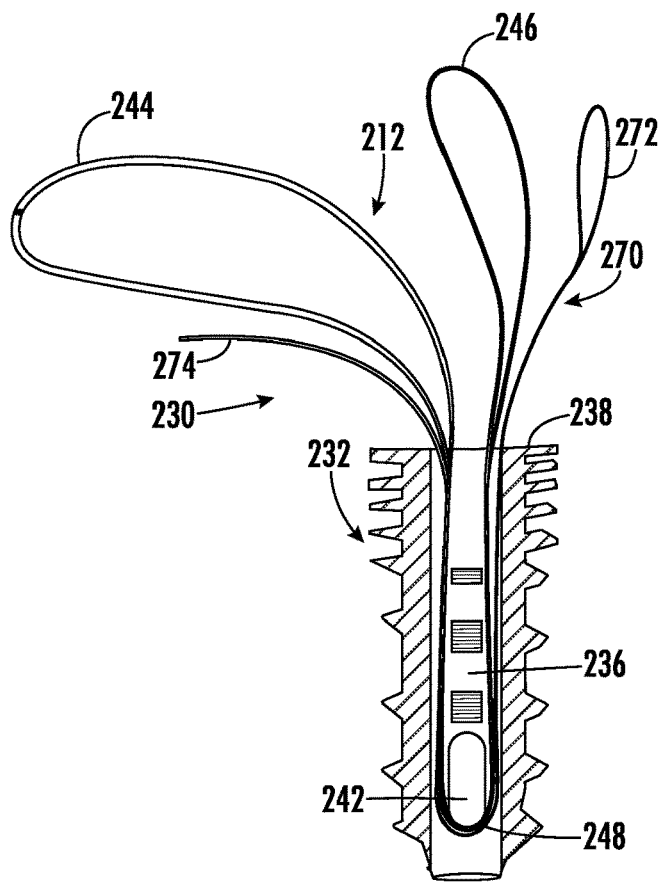
FIG. 10A represents a suture anchor assembly according to one example.
Figure 10B:
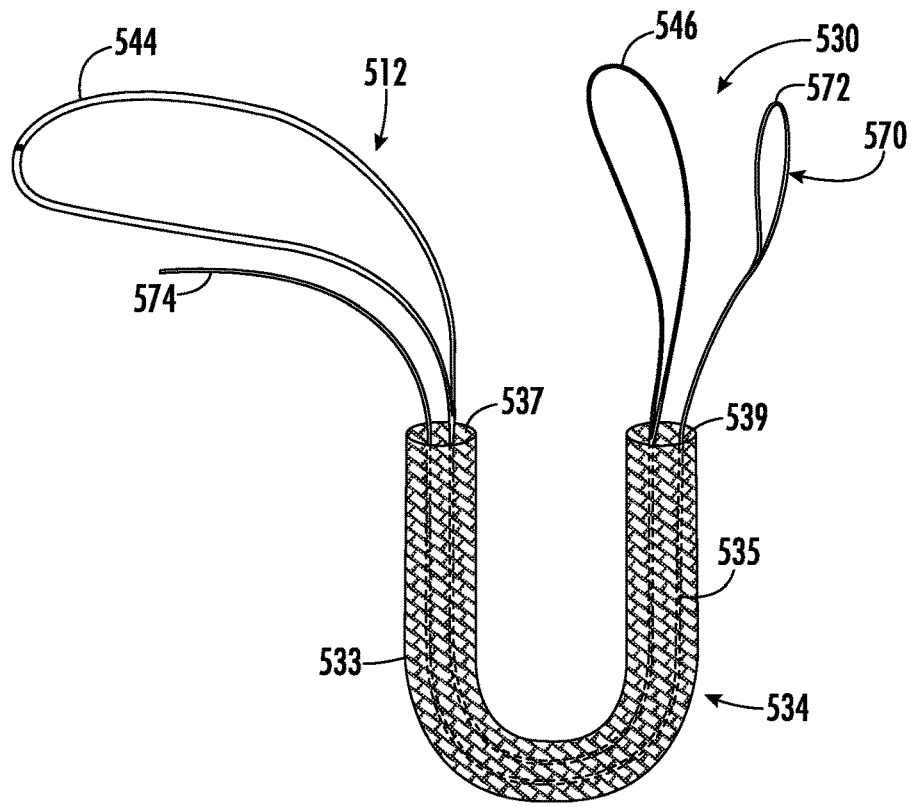
FIG. 10B represents a suture anchor assembly according to another example.

FIG. 10b shows an alternate suture assembly 430 including a soft, all suture anchor 432, rather than the hard anchor 32 of FIG. 4A. Suture loop 412, which may have the same structure as loop 12 in FIG. 1, loop 112 in FIG. 2, or loop 212 in FIG. 3, is woven through or otherwise embedded in a collapsible woven tube or sleeve 434, similar to the sleeves found in the Bio-met Juggerknotless® and other commercially available all suture knotless suture anchors. The sleeve 434, which is made of the same material as, and may be integral with, the suture loop 412, is bent into a U-shape having a first side 433, second side 435, and two proximal openings 437, 439. The suture loop 412 has been doubled on itself to form a first end bight 444, second end bight 446, and is embedded in the sleeve 434 such that the first end bight 444 extends proximally through the first proximal opening 437 in the first side 433, and the second end bight 446 extends proximally through the second proximal opening 439 in the second side 435. When the all suture anchor 432 is inserted in a pre-drilled hole in a bone and the end bights 444, 446 are pulled, the sleeve 434 collapses in the longitudinal direction and expands in a radial direction, exerting a contact force against the walls of the pre-drilled hole. An advantage of an all suture anchor 432 as shown in FIG. 4B is that it requires a smaller diameter hole than that required for the conventional hard anchor 32 of FIG. 4A.

Figure 5A:
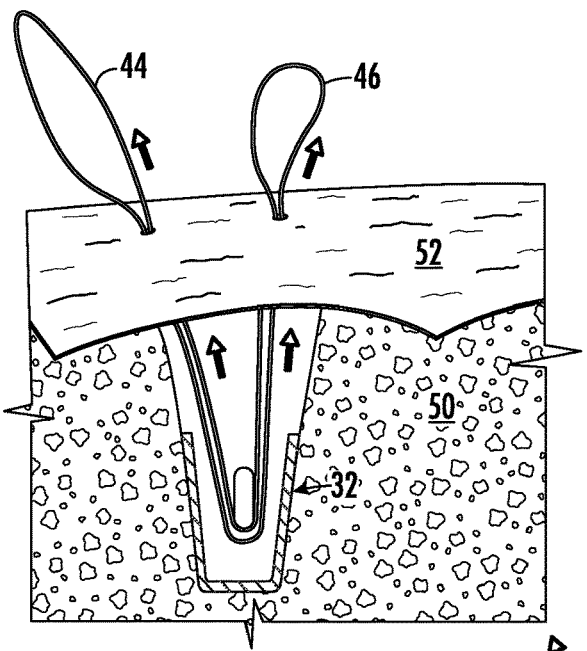
FIGS. 5A-D show a method of securing soft tissue to bone.
Figure 5B:
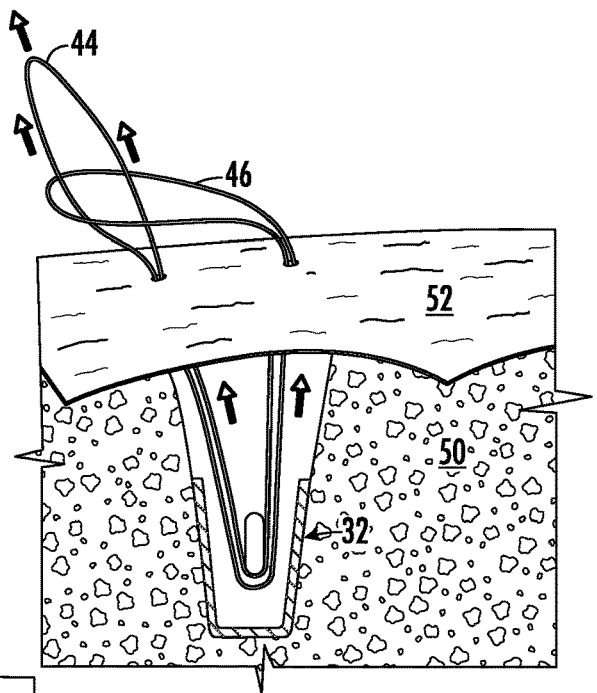
Figure 5C:
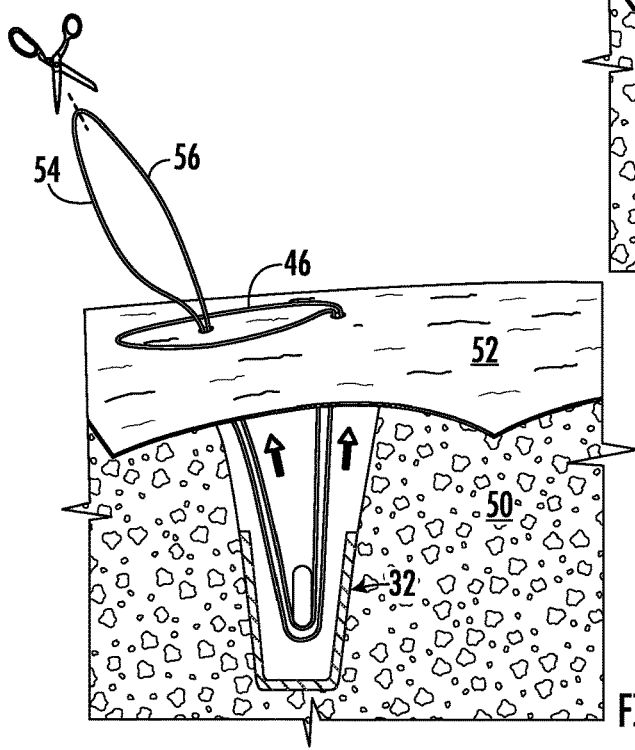
Figure 5D:
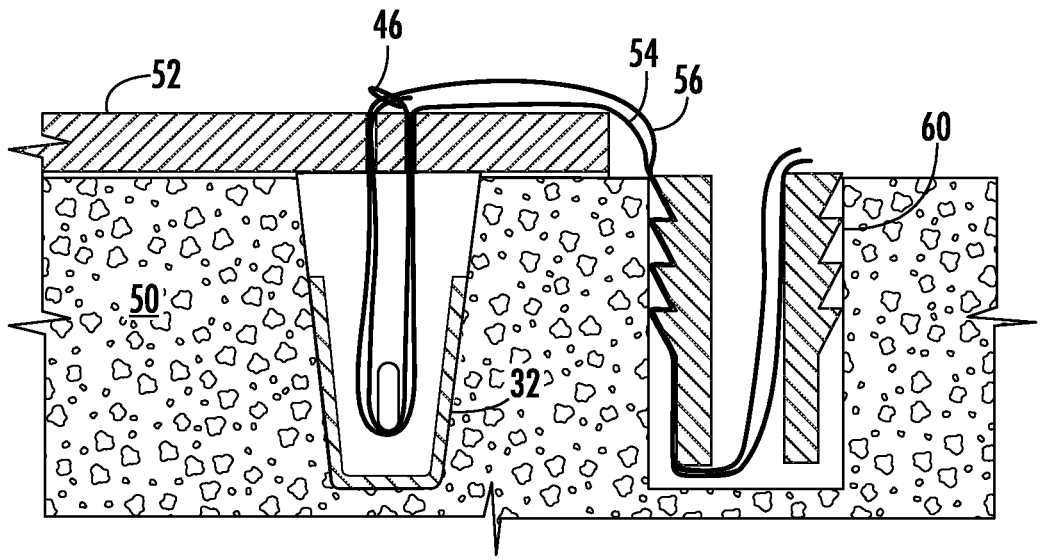

FIGS. 5A-D illustrate a knotless fixation technique which may be performed using the suture assembly 30 of FIG. 4A. Initially, the suture anchor 32 is implanted in a bone 50 such as, for instance, a humerus bone, beneath tissue 52 such as a rotator cuff tendon, and the end bights 44, 46 are passed in an upward direction through the tendon 52, as shown in FIG. 5A. Next, the first end bight 44 of the suture loop 12 is passed through the second end bight 46 to create a luggage tag configuration, as shown in FIG. 5B. The first end bight 44 is pulled upwardly until the second end bight 46 is flattened against the tendon 52, compressing the tendon against the bone 50, as shown in FIG. 5C. The surgeon may optionally cut through the first end bight 44, separating it into two distinct limbs 54, 56. The two limbs 54, 56, whether separated or not, are then inserted through the distal end of a second suture anchor 60 which is subsequently implanted in the bone 50, as shown in FIG. 5D. This traps the limbs 54, 56 in an interference fit between the anchor 60 and the bone 50 and holds the tendon 52 tightly in place against the bone 50.

Figure 6A:
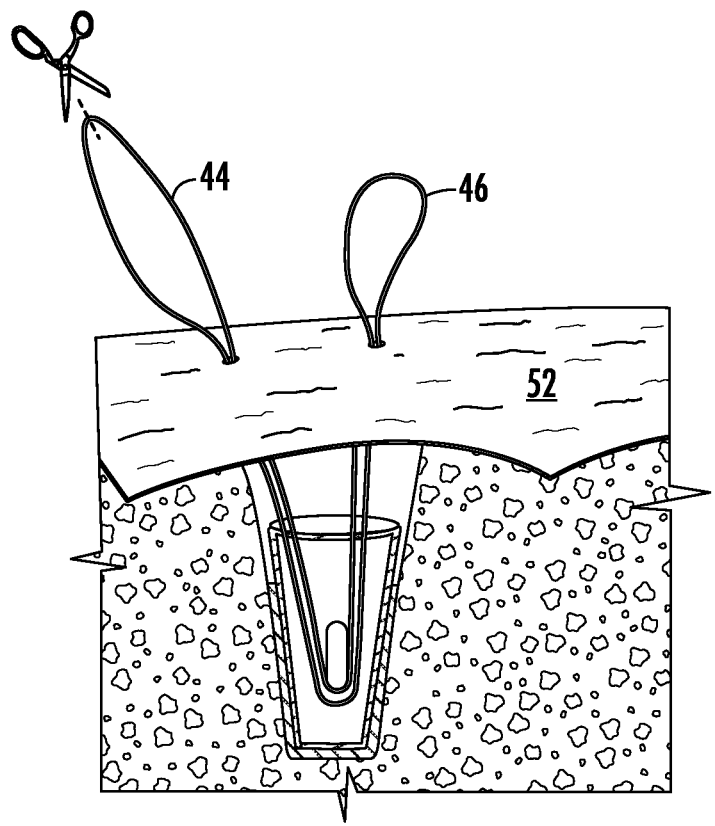
FIGS. 6A-C show an alternate method of securing soft tissue to bone.
Figure 6B:
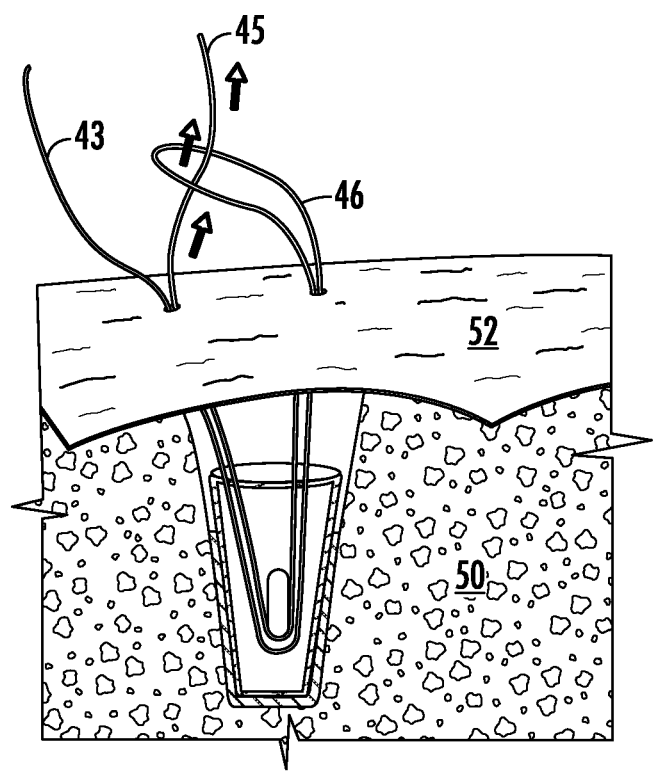
Figure 6C:
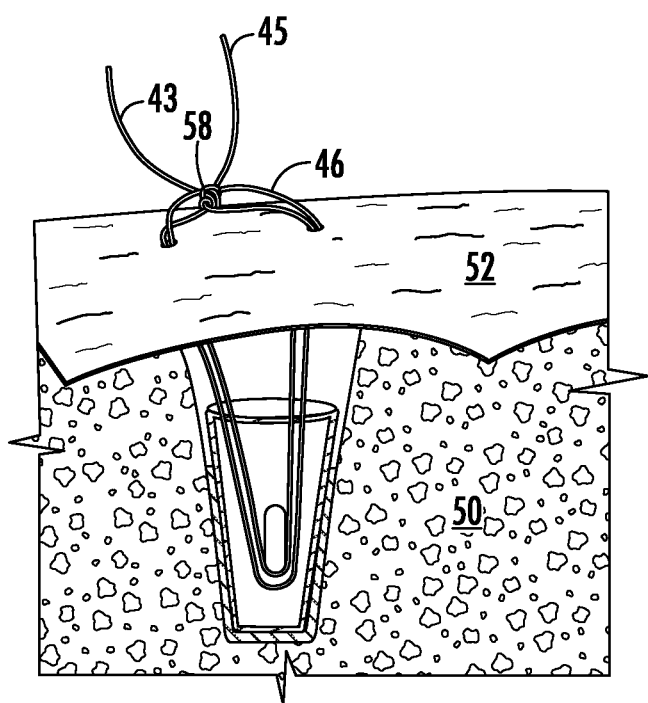

In an alternate technique, after the two end bights 44, 46 are inserted through two locations in the tendon 52, as shown in FIG. 6A, the surgeon cuts through the first end bight 44, separating it into two distinct limbs 43, 45, and one of the limbs 45 is inserted through the second end bight 46, as shown in FIG. 6B. The limbs 43, 45 are pulled until the second end bight 46 is flattened against the tendon 52, compressing the tendon 52 against the bone 50; and finally, the limbs 43, 45 are tied together using half-hitches or the like to form a knot 58, as shown in FIG. 6C. At this point, the limbs 43, 45 may either be trimmed or, if extra security is desired, inserted into a knotless anchor as shown in FIG. 5D.

The techniques illustrated in FIGS. 5A-D and 6A-C may be performed using any of the suture loops shown in FIGS. 1-3. If the varying-width loop of 212 of FIG. 3 is used, the first end bight 44 should include the thinner end 214 of the loop 212 and the second end bight 46 should include the thicker end 216 of the loop 212 since this will create greater interference with the anchor. Thus, the thicker end 216 forms a strong, secure base for the luggage tag, and the thinner end 214 has the easy manipulability desired for knot-tying.

In addition, the suture assembly 430 of FIG. 4B may be substituted for the suture assembly of FIG. 4A in the techniques of 5A-D and 6A-C. Use of an all suture anchor 432 may eliminate the need for steps 5D and 6C in these techniques, since the contact force exerted by the collapsed sleeve on the walls of the hole provides the same auxiliary locking function as the interference fit between the second suture anchor 60 and the bone 50 in FIG. 5D or the knot in FIG. 6C.

The techniques illustrated in FIGS. 5A-D and 6A-C may also be combined with other known techniques to provide a surgeon with a wide variety of options. For instance, the suture anchor may be loaded with multiple sutures to create luggage tag configurations at multiple fixation points between the bone and the tendon, and multiple anchors may be used to create double row suture bridges.

In some examples, second anchor 60 of FIG. 5D may be any type of commercially available knotless suture anchor such as the HEALIX ADVANCE™ knotless anchor by Depuy Synthes, or the PushLock™ and SwiveLock™ anchors by Arthrex. However, the fixation technique described in connection with FIG. 5D above holds the tendon more securely in place than the conventional knotless techniques normally used with these anchors, since the luggage tag configuration formed at the intersection between the second end bight 46 and the limbs 54, 56 of the first end bight acts as a stop preventing the tendon 46 from sliding relative to the suture. A knot 58 as shown in FIG. 6C adds even greater security.

Figure 7:
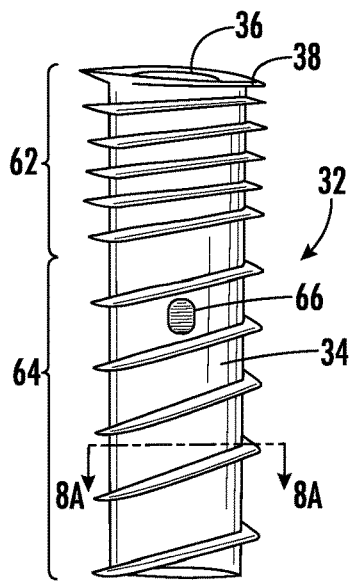
FIG. 7 shows an example of a suture anchor.
Figure 8A:
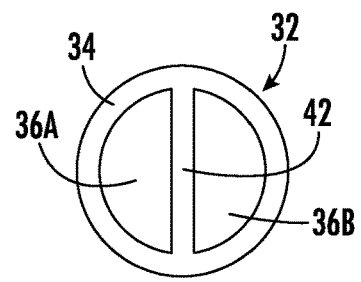
FIG. 8A shows a sectional view taken through line 8A-8A of FIG. 7.

FIG. 7 shows one example of suture anchor 32, which includes anchor body 34, inner cannulation 36, open proximal end 38, and blunt distal end 40. The anchor body 34 is double threaded, with a proximal portion 62 having a relatively small pitch and small thread diameter to core diameter ratio, giving it good purchase in cortical bone, and a distal portion 64 having a larger pitch and larger thread diameter to core diameter ratio, giving it good purchase in cancellous bone. A single vent 66 in the anchor body 34 allows bone marrow and associated stem cells to access the tendon or other soft tissue being repaired, thus promoting better healing. Suture bridge 42 extends across the inner cannulation, dividing the cross sectional area of the inner cannulation into two equally-sized sections 36A, 36B, as shown in FIG. 8A.

Figure 8B:
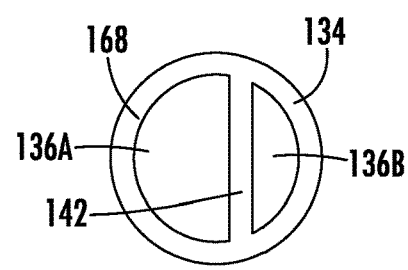
FIG. 8B shows a sectional view of a suture anchor according to an alternate example.

In an alternate example, a suture bridge 142 may be located in an off-center position, dividing the inner cannulation into a larger portion 136A and a smaller portion 136B, as shown in FIG. 8B. The cross-sectional area of the smaller portion 136B may, for instance, be about 40% of the cross-sectional area of the entire inner cannulation, and the cross-sectional area of the larger portion 136A may be about 60% of the cross-sectional area of the entire inner cannulation. This off-center location of the suture bridge may reduce slippage of the suture, since the tight spacing in the smaller portion results in increased frictional forces between the suture bridge 142, suture, and the inner side wall 168 of the anchor body 134. When the wider end of the varying width loop suture of FIG. 3 resides in the smaller portion 136B of the inner cannulation of the suture anchor, an especially strong interference fit is achieved.

Figure 9:
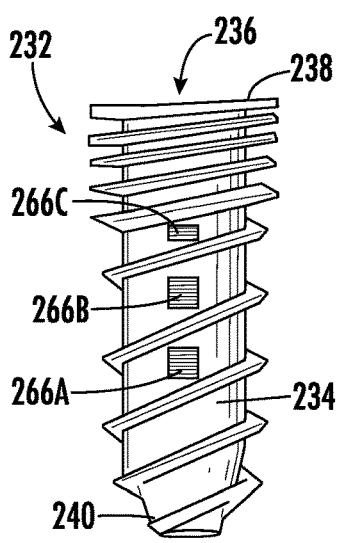
FIG. 9 shows an exterior view of a suture anchor according to another example.

In another example, shown in FIG. 9, a suture anchor 232 includes a double-threaded anchor body 234 having an inner cannulation 236 and open proximal end 238 similar to the suture anchor 32 of FIG. 7, but with a tapered distal tip 240 and three vents 266A,B,C. The tapered tip 240 facilitates penetration into bone, and the additional vents 266A,B,C allow for more bone marrow and stem cells to access the tendon, promoting even better healing. Suture anchor 232 also includes an internal suture bridge, which may be either centered, as in the example of FIG. 8A, or off to one side, as in the example of FIG. 8B.

FIG. 10A shows an example of a suture assembly 230 comprising the suture anchor 232 of FIG. 9, the varying-width suture loop 212 of FIG. 3, and a linking suture 270 comprising a looped end 272 and a straight end 274. The suture loop 212 has been doubled on itself to form a first end bight 244, second end bight 246, and a central bight 248, and positioned in the inner cannulation 236 of the anchor 232 such that each of the end bights 244, 246 extends in a proximal direction through the open proximal end 238 of the anchor and the central bight 248 extends around the suture bridge 242. The linking suture 270 has also been doubled on itself and positioned in the inner cannulation such that its looped end 272 extends proximally through the open proximal end of the anchor 232 on the same side of the anchor bridge 242 as the thin second end bight 246 of suture loop 212, and its straight end 274 extends proximally through the open proximal end of the anchor 232 on the same side of the anchor bridge 242 as the thick first end bight 244 of suture loop 212.

In other examples of suture assemblies, the varying-width suture loop 212 could be replaced with either the thin suture loop 12 of FIG. 1 or the suture tape loop 112 of FIG. 2. In addition, the linking suture 270 could be replaced with any of suture loops 12, 112, or 212.

FIG. 10B shows an all suture version of a suture assembly 530 wherein a varying-width suture loop 512 and linking suture 570 are embedded in a collapsible tube or sleeve 534 similar to the sleeve shown and described in connection with FIG. 4B. The first end bight 544 of the suture loop 512 extends proximally through a first opening 537 in the first side 533 of the sleeve 534, and the second end bight 546 of the suture loop 512 extends proximally through a second opening 539 in the second side 535 of the sleeve 534. The straight end 574 of the linking suture 570 extends through the first opening 537, together with the first end bight 544 of the suture loop 512, and the looped end 572 of the linking suture 270 extends through the second opening 539, together with the second end bight 546 of the suture loop 512.

Figure 11A:
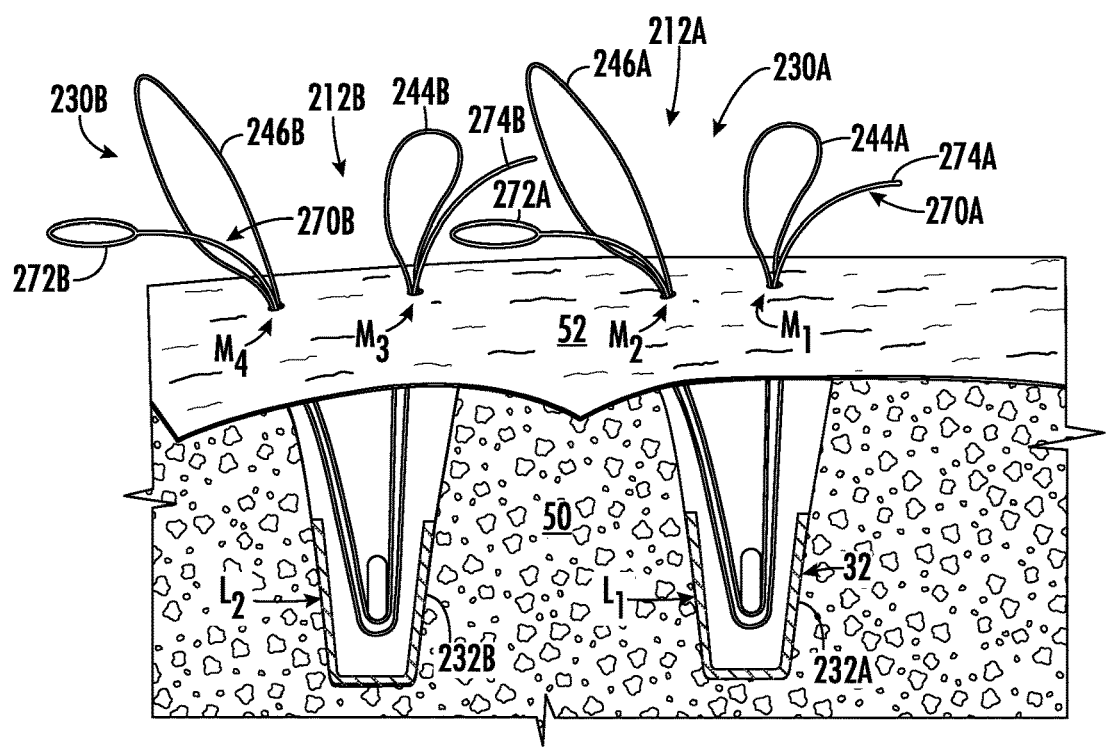
FIGS. 11A-E show a double-row method of securing soft tissue to bone.

FIGS. 11A-E illustrate a double row suture technique using two suture assemblies 230A,B. Initially, as shown in FIG. 11A, the anchor 232A of a first suture assembly 230A is implanted in a first location $L_1$ in a bone 50 such as a humerus, and the anchor 232B of a second suture assembly 230B is implanted in the bone 50 in a second location $L_2$ which defines a medial row with the first location $L_1$. The second suture assembly 230b is implanted in the same orientation as the first suture assembly 230, so that the straight end 274B of the linking suture 270B of the second suture assembly 230B faces the looped end 272A of the linking suture 270A of the first suture assembly 230A. The first, thicker, end bight 244A of the suture loop 212A of the first suture assembly 230A and the straight end 274A of the linking suture 270A of the first suture assembly 230 are passed upwardly through a first location $M_1$ in a tissue 52 such as a rotator cuff tendon above the bone 50. The second, thinner, end bight 246A of the suture loop 212A of the first suture assembly 230A and the looped end 272A of the linking suture 270A of the first suture assembly 230 are passed upwardly through a second location $M_2$ in the tissue 52. The first, thicker, end bight 244B of the suture loop 212B of the second suture assembly 230B and the straight end 274B of the linking suture 270B of the second suture assembly 230B are passed upwardly through a third location $M_3$ in the tissue 52. The second, thinner, end bight 244B of the suture loop 212B of the second suture assembly 230B and the looped end 272B of the linking suture 270B of the second suture assembly 230B are passed upwardly through a fourth location $M_4$ in the tissue 52.

Figure 11B:
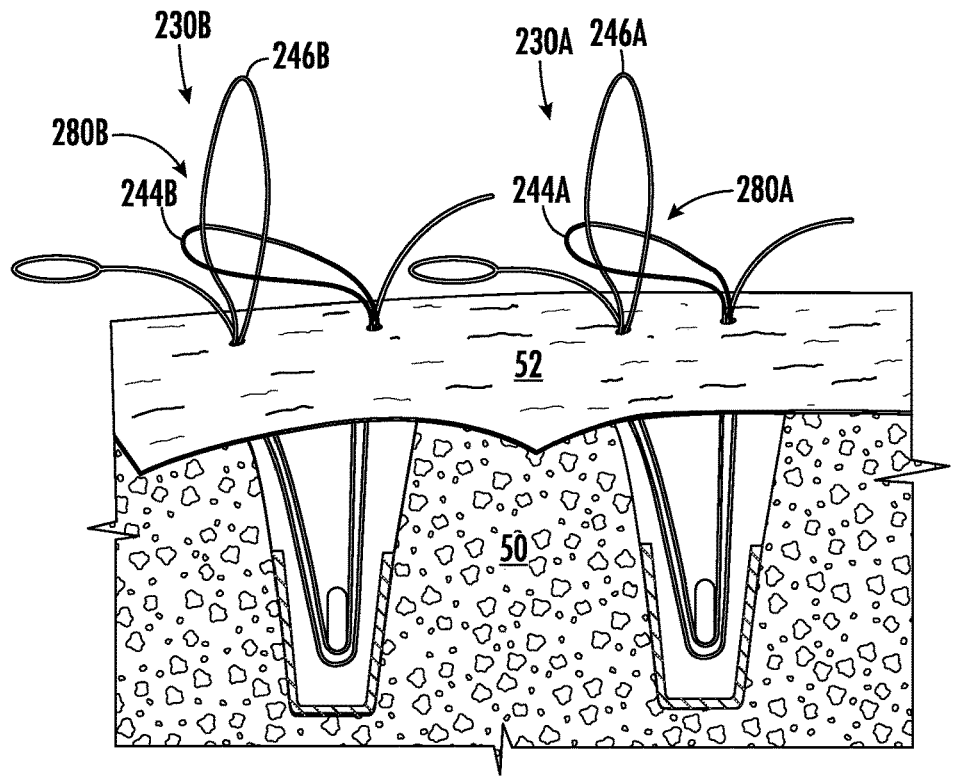

Next, the second end bight 246A of the suture loop 212A of the first suture assembly 230A is pulled through the first end bight 244A of the suture loop 212A of the first suture assembly 230A to form a first luggage tag configuration 280A, and the second end bight 246B of the suture loop 212B of the second suture assembly 230B is pulled through the first end bight 244B of the suture loop 212B of the second suture assembly 230B to form a second luggage tag configuration 280B as shown in FIG. 11B.

Figure 11C:
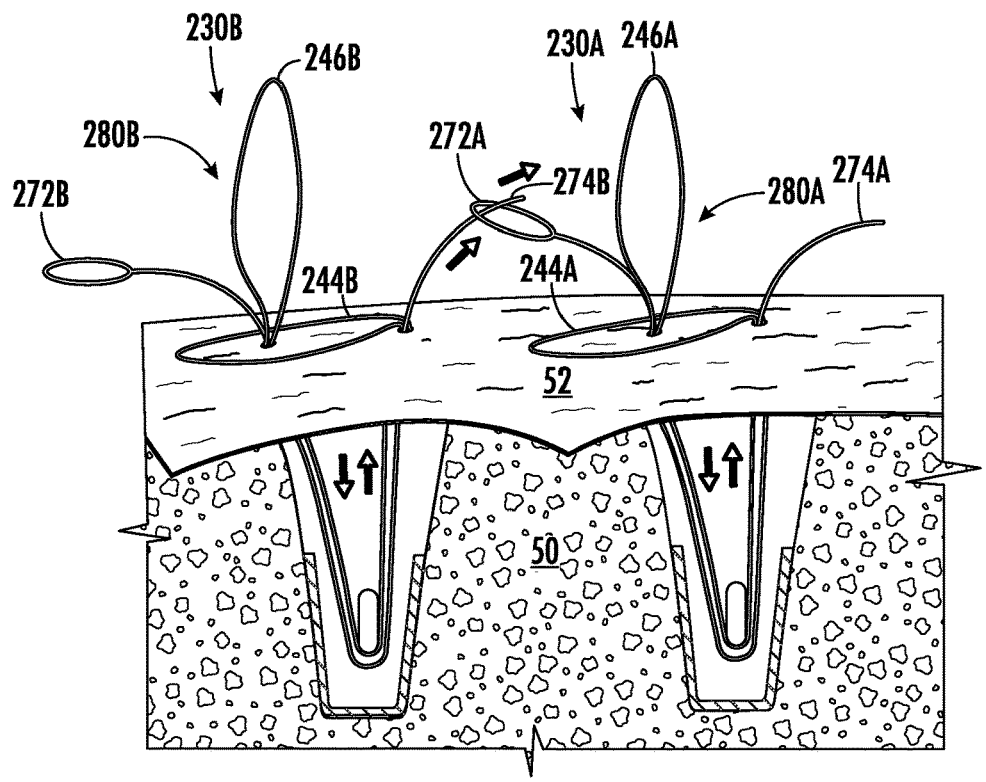
Figure 11D:
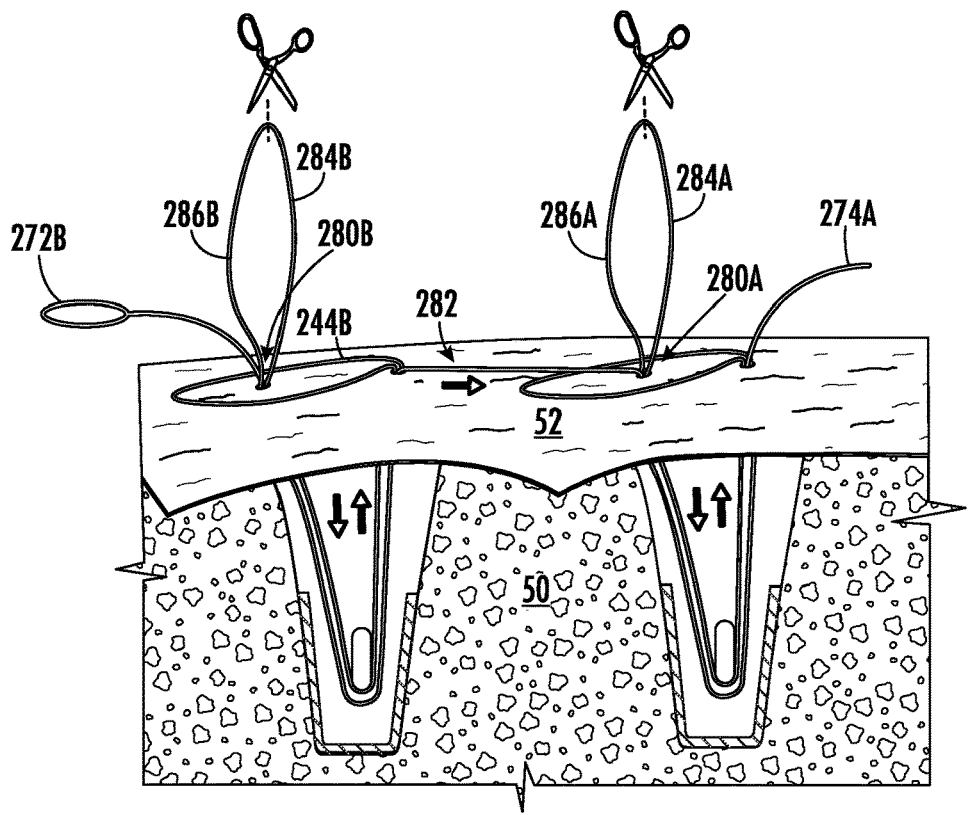

The second end bights 246A,B are pulled until the first end bights 244A, B are flattened against the tissue 52, as seen in FIG. 11C. The straight end 274B of the linking suture of the second suture assembly 230B is then inserted through the looped end 272A of the linking suture of the first suture assembly 230A, and the straight end 274A of the linking suture of the first suture assembly 230 is pulled upwardly, drawing the straight end 274B of the linking suture of the second suture assembly 230B down through the tendon 52, and creating a medial bar 282 joining the two luggage tags 280A, 280B, as shown in FIG. 8D. The apex of each second suture loop 246A,B is then cut, dividing the second suture loop 246A of the first suture assembly 230A into two free limbs 284A, 286A, and the second suture loop 246B of the second suture assembly 230B into two free limbs 284B, 286B.

Figure 11E:
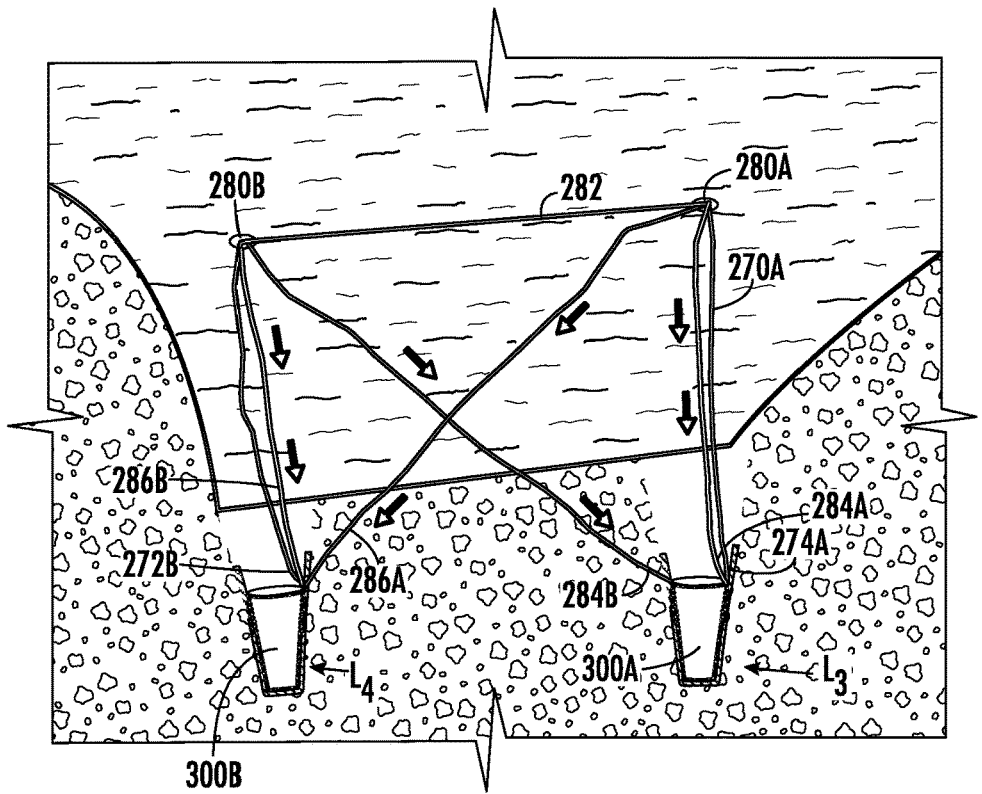

In the final steps, illustrated in FIG. 11E, the straight end 274A of the linking suture 270A of the first suture assembly, one free limb 284A of the suture loop of the first suture assembly, and one free limb 284B of the suture loop of the second suture assembly are inserted into or through the distal end of a first lateral anchor 300A, which is then implanted in a first lateral location L₃ in the bone 50, retaining the ends 274A, 284A, and 284B in an interference fit between the exterior of the anchor 300A and the bone 50. The looped end 272B of the second suture assembly, the remaining free limb 286A suture loop of the second suture assembly, and the remaining free limb 286B of the suture loop of the first suture assembly are inserted into or through the distal end of a second lateral anchor 300B, which is then implanted in a second lateral location L₄ in the bone 50, retaining the ends 272B, 286A, and 286B in an interference fit between the exterior of the anchor 300B and the bone 50.

The varying-width suture loops 212A,B used in the method of FIGS. 11A-E may be replaced by wire suture loops of the type shown in FIG. 1, or suture tape loops shown in FIG. 2. Alternatively, the method of FIGS. 11A-E may be performed using the all suture anchor assembly 530 of FIG. 10B rather than the hard suture anchor assembly 230 of FIG. 10A.

FIGS. 12-16 show a lateral anchor 300 useable in the method of FIGS. 5A-D and 6A-C as well as in the method of FIGS. 11A-E. The lateral anchor 300 includes a proximal anchor body 302 and a distal tip 304. The proximal anchor body 302 includes an inner cannulation 306 allowing it to slide along a tubular cylinder driver 308 having a closed proximal end 310 and an open distal end 312. A distal portion 313 of the inner cannulation 306 is internally threaded. A proximal portion of the inner cannulation 306 is hexagonal and accepts the distal portion of a ball end hex driver 314.

Figure 12:
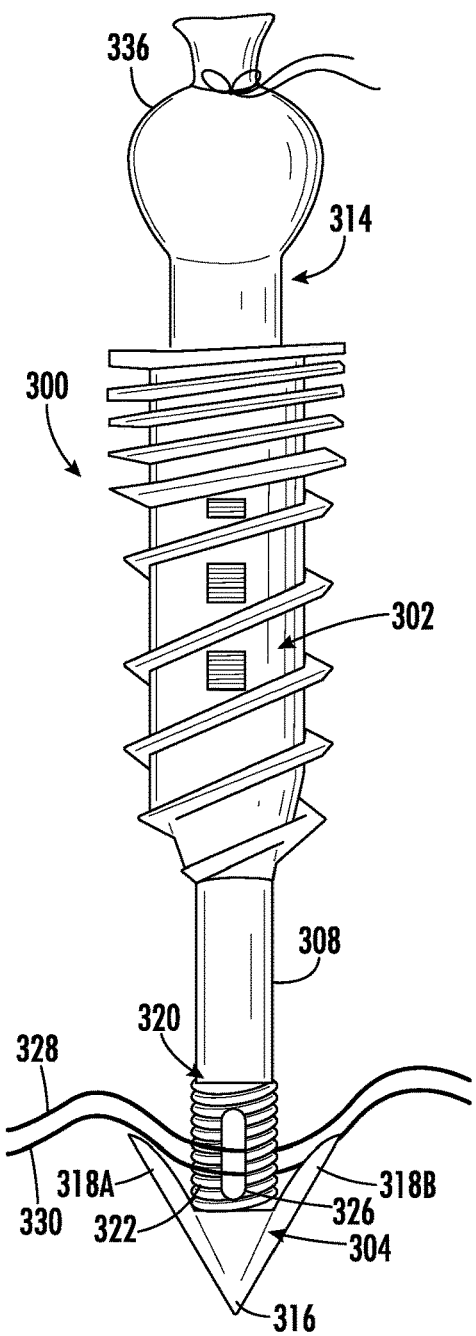
FIG. 12 is a front view of a lateral row suture anchor in a pre-deployed configuration.
Figure 13:
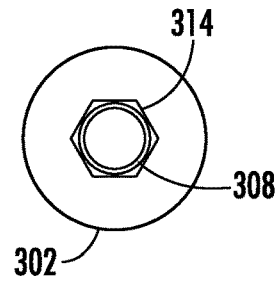
FIG. 13 is top view of the lateral row suture anchor of FIG. 12.
Figure 14:
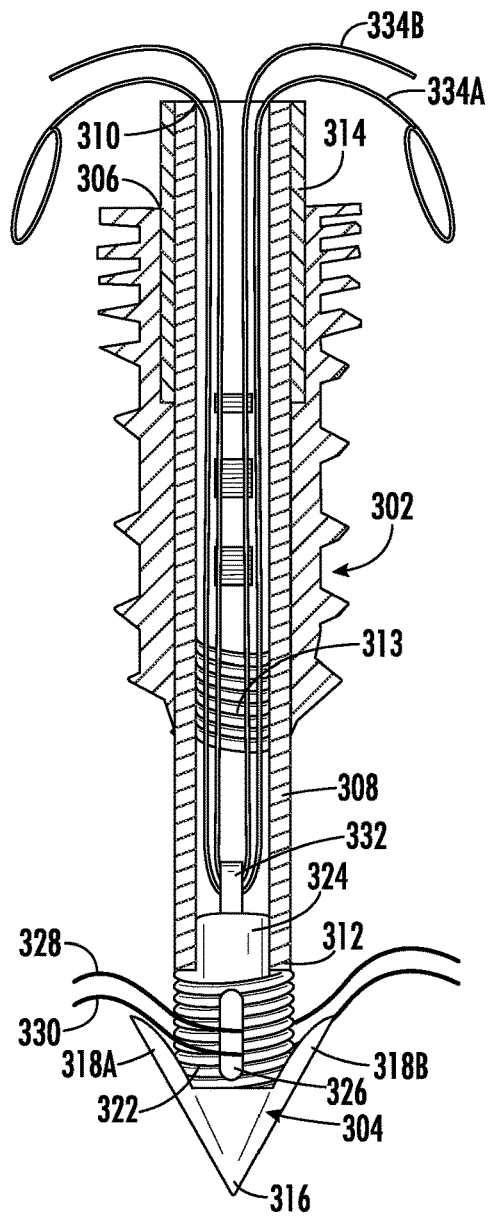
FIG. 14 is an internal view of the lateral row suture anchor of FIG. 12 in the pre-deployed configuration, with the handle of the hex driver removed for purposes of illustration.

The distal tip 304 includes a pointed distal end 316 to facilitate insertion into bone, and a pair of proximal spikes 318A,B which extend radially outwardly and proximally from the pointed distal end 316 to reduce the likelihood the likelihood of anchor pull-out. A proximally extending neck 320 is located radially inwardly of the spikes 318A,B. A distal portion 322 of the neck 320 is externally threaded, and a narrower proximal portion 324 extends into the open distal end 312 of the cylinder driver 308. An eyelet 326 provided in the externally threaded distal portion 322 of the neck 320 receives the free ends of repair sutures 328, 330 from the medial row. An apertured tab 332 is provided at the proximal end of the neck 324 for receiving first and second stay sutures 334A,B that extend through the concentric interiors of anchor body 302, cylinder driver 308, and hex driver 314. For purposes of illustration, the stay sutures 334A,B have been shown in FIG. 14 to extend freely out from the proximal end of the cylinder driver shaft 308, but in practice, they would be tied together on top of the ball-shaped proximal end 336 of ball end hex driver 314, as shown in FIG. 12, holding the distal tip 304 in place until implantation is complete.

Figure 15:
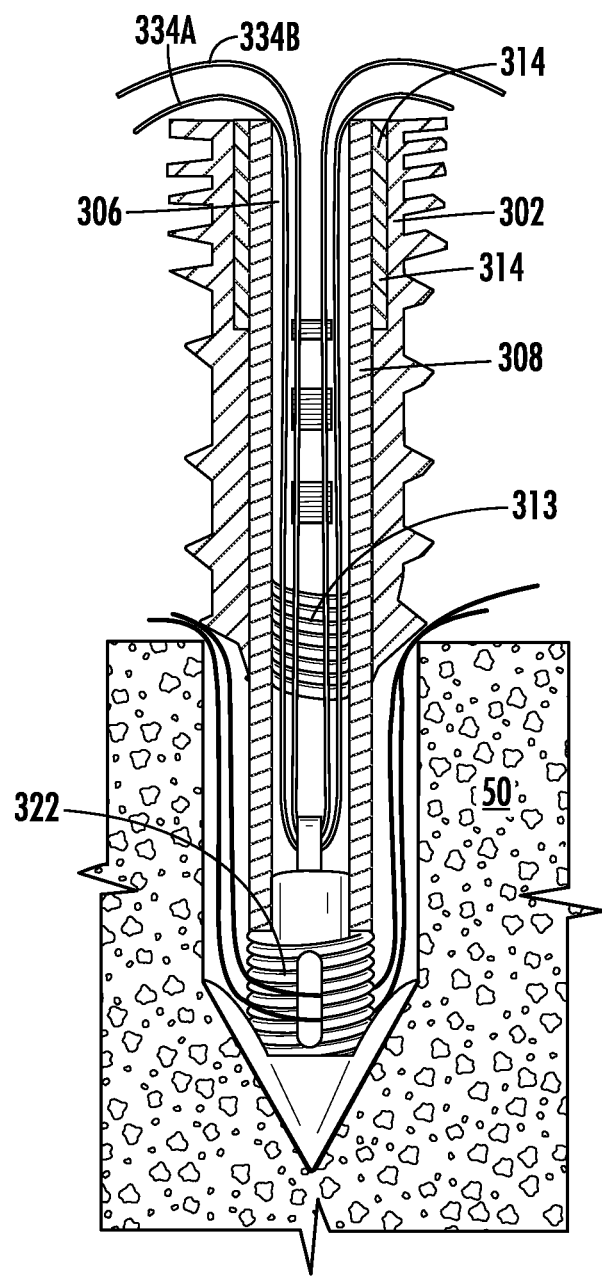
FIG. 15 is an internal view similar to FIG. 14, showing the lateral row suture anchor in a partially deployed configuration.

After the repair sutures 328, 330 have been inserted through the eyelet 326 in the distal tip 304, the surgeon taps or pounds on the closed proximal end 310 of cylinder driver 308, causing the pointed distal end 316 of the distal tip to penetrate the bone. When the distal thread of the proximal anchor body 302 engages the bone 50, as shown in FIG. 15, the surgeon rotates the hex driver 314, screwing the proximal anchor body 302 deeper into the bone.

Figure 16:
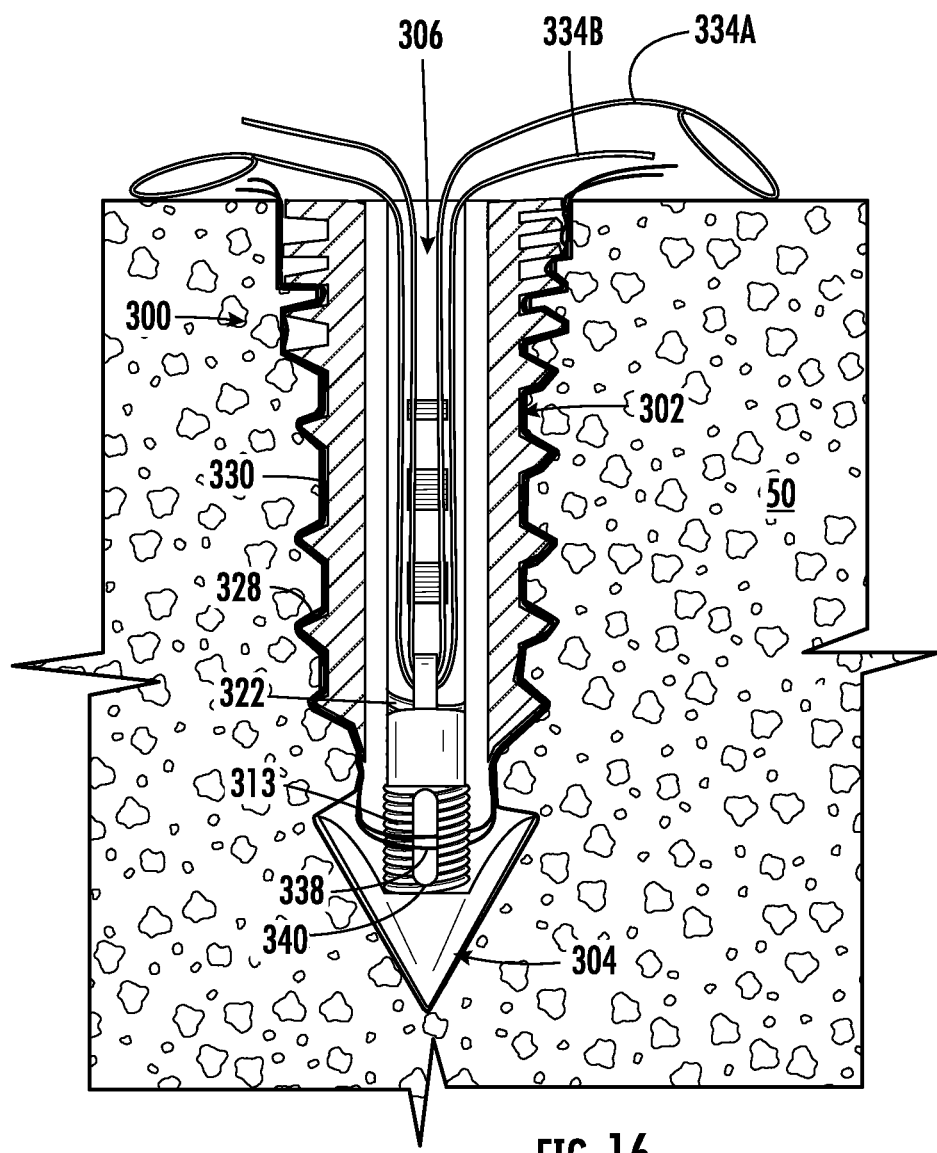
FIG. 16 is an internal view of lateral suture anchor of FIGS. 12-15 in a fully deployed configuration, after removal of the cylinder and hex drivers.

Continued rotation of the hex driver causes the internally threaded distal portion 313 of the inner cannulation 306 of the proximal anchor body 302 to reach and engage the externally threaded proximal portion 322 of the distal tip 304, locking the proximal anchor body 302 and the distal tip 304 together. At this point, the ends of the stay sutures 328, 330 are untied, and both the ball end hex driver and the cylinder driver are withdrawn from the anchor 300, as shown in FIG. 16. The repair sutures 328, 330 are now trapped between the bone 50 and the anchor 300, as well as between the distal end 338 of the proximal anchor body 302 and the distal end 340 of the eyelet 326 in the distal tip 304. The stay sutures 34A,B are available for use as needed to augment the strength of a repair after the lateral anchor 300 has been placed, and to prevent or reduce and stabilize dog-ear lesions which might otherwise interfere with healing.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A suture assembly comprising:
   a medial anchor having a first side, a second side, and a proximal end;
   a repair suture formed as a continuous loop and doubled on itself to form a first end bight, a second end bight and a central bight, and positioned in the medial anchor such that the first end bight extends out of the proximal end of the medial anchor on the first side thereof, and the second end bight extends out of the proximal end of the medial anchor on the second side thereof; and
   a linking suture having a looped end joined to a straight end by an intermediate portion, the linking suture doubled on itself and positioned in the medial anchor such that the straight end extends out of the proximal end of the medial anchor on the first side thereof, and the looped end extends out of the proximal end of the medial anchor on the second side thereof.

2. A suture assembly according to claim 1, wherein:

the repair suture is formed from a strand of suture material and includes a first end, a second end, and two sides extending between the first and second ends; and the strand has a thickness which increases from a minimum thickness at the first end to a maximum thickness at the second end.

3. A suture assembly according to claim 2, wherein:

the proximal end of the medial anchor is open and communicates with an inner cannulation;

the medial anchor further comprises a suture engagement feature that extends across the inner cannulation at a predetermined location;

the inner cannulation has a predetermined first cross-sectional area at the predetermined location; and the inner suture engagement feature divides the inner cannulation into a first portion having a second cross-sectional area and a second portion having a third cross-sectional area;

wherein the second cross-sectional area is about 60% of the first cross-sectional area and the third cross-sectional area is about 40% of the first cross-sectional area; and wherein the suture loop is locked into the suture anchor by an interference fit between the maximum thickness of the strand and the third portion of the inner cannulation portion at the predetermined location.

4. A suture anchor according to claim 2, wherein:

the repair suture and linking suture extend through an all suture anchor having a first opening located in the first side, a second opening located in the second side, and a central bight;

the first end bight of the repair suture extends proximally through the first opening in the all suture anchor;

the second end bight of the repair suture extends proximally through the second opening in the all suture anchor;

the straight end of the linking suture extends though the first opening in the all suture anchor; and the looped end of the linking suture extends through the second opening in the all suture anchor.

5. A method for attaching tissue to bone, comprising:

implanting a first suture assembly according to claim 1 in a first medial location in a bone below a detached tissue;

implanting a second suture assembly according to claim 1 in a second medial location in the bone, with the looped end of the linking suture of the second suture assembly facing the straight end of the linking suture of the first suture assembly;

passing the first end bight of the repair suture of the first suture assembly and the straight end of the linking suture of the first suture assembly through a first location in the tissue;

passing the second end bight of the repair suture of the first suture assembly and the looped end of the first suture assembly through a second location in the tissue;

passing the first end bight of the repair suture of the second suture assembly and the straight end of the linking suture of the second suture assembly through a third location in the tissue;

passing the second end bight of the repair suture of the second suture assembly and the looped end of the second suture assembly through a fourth location in the tissue;

passing the first end bight of the repair suture of the first suture assembly through the second end bight of the repair suture of the first suture assembly to form a first luggage tag configuration;

passing the first end bight of the repair suture of the second suture assembly through the second bight of the repair suture of the second suture assembly to form a first luggage tag configuration;

passing the straight end of the linking suture of the second suture assembly through the looped end of the first suture assembly;

pulling the straight end of the linking suture of the first suture assembly to draw the straight end of the linking suture of the second suture assembly through the tissue at the second location and create a medial bar connecting the second and third locations;

cutting through the first end bight in the first luggage tag configuration to create a first limb end and a second free limb;

cutting through the first end bight in the second luggage tag configuration to create a third free limb and a fourth free limb;

inserting the straight end of the linking suture of the first suture assembly, the first free limb, and the third free limb into a retaining feature in a first lateral anchor;

inserting the looped end of the linking suture of the second suture assembly, the second free limb, and the fourth free limb into a retaining feature in a second lateral anchor;

implanting the first lateral anchor in a first lateral location in the bone; and implanting the second lateral anchor in a second lateral location in the bone.

6. The method of claim 5, wherein:

each repair suture is formed from a strand of suture material and includes a first end, a second end, and two sides extending between the first and second ends; and the strand has a thickness which increases from a minimum thickness at the first end to a maximum thickness at the second end.

7. The method of claim 5, wherein the maximum thickness of the strand is located in the first end bight.

8. The method of claim 5, wherein the second suture assembly is positioned such that the free end of the linking suture of the second suture assembly faces the looped end of the linking suture of the first suture assembly.

9. The method of claim 5, wherein the first lateral anchor comprises:

a proximal anchor body having
 an inner cannulation;
 an open proximal end; and
 an open distal end;
a distal tip having
 a retaining feature configured to receive the straight end of the linking suture of the first suture assembly, the first free end, and the third free end,
 a suture engagement feature configured to engage a pair of stay sutures; and
internal locking elements configured to lock the distal tip to the proximal anchor body when the lateral anchor is implanted in a bone.

10. The method of claim 9, wherein the distal tip includes:

a pointed distal end configured to facilitate insertion into bone; and a pair of spikes extending proximally and radially outwardly from the pointed distal end.

11. The method of claim 9, wherein the internal locking elements comprise mating screw threads formed in a distal portion of the inner cannulation of the proximal anchor body and on a proximal portion of the distal tip.

* * * * *